United States Patent [19]

Rouse et al.

[11] 4,304,134

[45] Dec. 8, 1981

[54] APPARATUS FOR ULTRASONICALLY INSPECTING CIRCULAR BORES

[75] Inventors: Marshall J. Rouse, Waxhaw; Colon K. Ange, Charlotte, both of N.C.

[73] Assignee: Westinghouse Electric Corp., Pittsburgh, Pa.

[21] Appl. No.: 147,801

[22] Filed: May 8, 1980

[51] Int. Cl.³ .............................................. G01N 29/04
[52] U.S. Cl. ...................................... 73/634; 324/220
[58] Field of Search ................. 73/623, 633, 634, 637, 73/640, 641; 324/220

[56] References Cited

U.S. PATENT DOCUMENTS

| | | | |
|---|---|---|---|
| 3,238,448 | 3/1966 | Wood et al. | 324/220 |
| 3,952,581 | 4/1976 | Gottelt | 73/641 X |
| 3,960,006 | 6/1976 | Smith . | |
| 4,105,972 | 8/1978 | Smith | 324/220 |

FOREIGN PATENT DOCUMENTS

| | | | |
|---|---|---|---|
| 631988 | 11/1949 | United Kingdom | 324/220 |
| 627396 | 10/1978 | U.S.S.R. | 73/633 |

*Primary Examiner*—James J. Gill
*Attorney, Agent, or Firm*—F. J. Baehr, Jr.

[57] ABSTRACT

Apparatus for ultrasonically inspecting material radially bounding a circular bore into which the apparatus is insertable. The apparatus includes a central housing adapted to lie along the bore's longitudinal axis, three support arms which are engageable with the bounding wall of the bore and are circumferentially equally spaced about the central housing, linkage arms joining the support arms and the central housing for maintaining a predetermined relative configuration between the support arms and the bore wall, a transducer carrier which protrudes radially inside the support arms' engageable surfaces and is supported by each support arm, an ultrasonic transducer carried in each ultrasonic transducer carrier, means for biasing the transducers radially outward relative to their associated transducer carrier, and a pneumatically actuated cylinder which rotates the linkage arms and displaces the support arms radially outward into engagement with the bore wall. The transducers are restrained in the transducer carriers within predetermined displacement limits by a pin extending from each transducer carrier into an opening formed in each transducer. The transducers' openings are radially larger than the pins extending thereinto so as to permit limited radial displacement of the transducers relative to the carriers. Suitable relative radial positioning of the transducer carriers and support arms and selection of appropriate strength biasing means enables application of high centering forces on the support arms to coaxially align the housing with the bore's center line while independently providing relatively small, optimum engagement forces between the transducers and bore wall.

10 Claims, 2 Drawing Figures

APPARATUS FOR ULTRASONICALLY INSPECTING CIRCULAR BORES

BACKGROUND OF THE INVENTION

This invention relates to ultrasonic inspection of materials bounding circular bores and, more particularly, to boresonic inspection apparatus having bore centering features and transducer carrying devices which are insertable in the bores.

Steam turbine rotors are often circularly bored for purposes which include removal of inclusions and impurities inherently induced by metal casting processes and to reduce the time necessary for heating the rotor to a substantially constant temperature across its radial dimension when steam is introduced on the radial outside thereof. To insure high reliability and continuous turbine operation inspection procedures are periodically scheduled for the purposes of detecting damage to components and affecting repairs to prevent damage resulting from failure of those components. Inspection of the turbine rotor for cracks, defects, and other imperfections has become an important part of such inspection procedures. Ultrasonic inspection from inside the rotor bore presently constitutes a popular inspection process due to its precision, ease of implementation, and speed.

Heretofore, ultrasonic transducers of various types were affixed to a support device which was inserted in the rotor bores and radially expanded to engage the transducers with the bore walls. The support devices provided a self-centering action by simultaneously radially displacing three circumferentially equally spaced transducers into contact with the bore wall. The three transducers were circumferentially rotated at selected axial positions about the bore's longitudinal centerline during engagement with the bore wall. Such inspection procedures often included ultrasonically inspecting each of the selected axial locations with ultrasonic transducers having specialized capabilities such as detection of radial cracks, longitudinal cracks, and circumferential cracks. Since the ultrasonic transducers, by their nature, necessarily contacted the bore wall, the transducers were radially engaged with the bore wall by the self-centering action. The transducers thus provided the means for inspection and constituted the support device's bore wall engaging member. It has been found that proper self-centering action obtains when a force level of 50–100 pounds is exerted on the bore wall by each of the three bore wall engaging transducers. It has also been found that a substantially lesser engagement force of between 5 and 10 pounds on each transducer is optimum from an ultrasonic standpoint to minimize the error in back wall ultrasonic reflections. Exertion of such centering forces directly on the transducer sometimes squeezed sonic coupling material (often an oil film) away from the transducer lens so as to cause an inaccurate or incomplete indication of the inspected material content. Furthermore, squeezing the ultrasonic coupling material away from the transducer lens and simultaneously rotating the transducers sometimes damaged the transducers resulting in lost time and expense in repairing or replacing the transducers.

SUMMARY OF THE INVENTION

In general, an ultrasonic inspection apparatus made in accordance with the present invention has a housing which is insertable in a bore along the bore's longitudinal axis, a plurality of linkage arms rotatably connected to the housing at selected circumferential locations, a plurality of support arm structures rotatably connected to the linkage arms and engageable with the bore wall, means for maintaining a desired relative configuration between the support arms and the bore wall for any radial position of the support arms, a plurality of instruments engageable with the bore wall, means joined to the support arm structures for carrying the instrument, means for biasing the instruments radially outward relative to the support arm structures, means for restraining the instrument's radial movement beyond a predetermined point, and means disposed in the housing for rotating the linkage arms.

Pins preferably provide the rotatable connections between the housing and linkage arms and between the linkage arms and the support arms. Each support arm includes a body portion to which the rotatable connections are made and at least one wheel rotatably joined to the body portion along the body portion's radially outside boundary with that wheel being engageable with the bore wall and having an axis of rotation parallel therewith so as to facilitate rotation of the support arms around the bore during their engagement with the bore wall. Radial extension of the support arms at equal rates provides a self-centering action to the housing within the bore and enables application of desired centering forces for engagement of the support arm structures and bore wall. Exclusive engagement between the wheel and the bore wall is assured by maintaining the wheel's axis of rotation parallel with the bore wall. Means for carrying the instrument preferably constitutes a structure which has a radially outermost extension less than the radially outermost protrusion of the support arm wheel. When the wheels are unengaged with the bore wall, the instruments protrude radially therebeyond so as to ensure engagement of the instruments with the bore wall when the wheels are engaged therewith. The carrier means positioning relative to the support arms and the biasing means' biasing force are cooperatively selected to provide application of engagement forces between the instrument and bore wall with those forces being independent of the centering forces engaging the support wheels with the bore wall. Forces for engaging the instruments such as transducers against the bore wall have optimum values which permit the presence therebetween of coupling material such as oil films, minimize transducer lens damage during rotation thereof during engagement with the bore wall, and reduce error in back wall ultrasonic reflections. The capability for applying transducer to bore wall engagement force levels independently of the self-centering force levels provides the aforementioned advantages by suitable adjustment of the carrier means position relative to the support arms, selection of appropriate biasing forces for the biasing means, and the radial length of the instrument such as the transducer.

BRIEF DESCRIPTION OF THE DRAWINGS

The objects and advantages of this invention will become more apparent from reading the following detail description in connection with the accompanying drawings, in which.

DESCRIPTION OF THE PREFERRED EMBODIMENT

Figure 1:
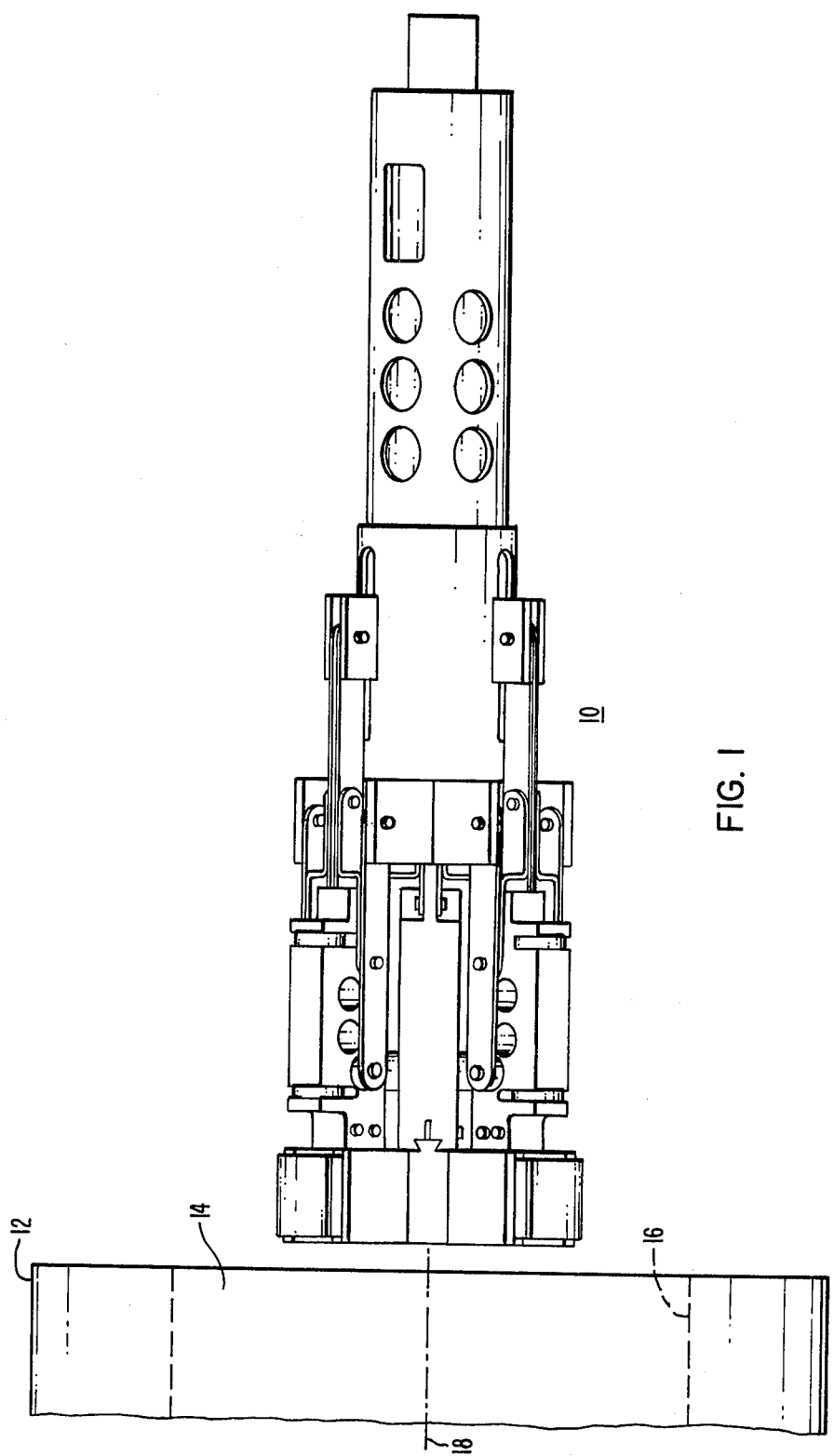
FIG. 1 is an elevation view of the present invention prior to its insertion in a circular bore.

Referring now to the drawings in detail wherein like reference numerals refer to like components, FIG. 1 shows the present invention inspection apparatus 10 coaxially aligned with rotor 12 and circular rotor bore 14 into which apparatus 10 is insertable. Circular bore 14 is bounded by bore wall 16 which is engageable by portions of apparatus 10 for the purposes of centering apparatus 10 in the bore and providing means for transmitting and/or receiving ultrasonic signals such as transducers. Ultrasonic signals reflected to the transducers may be interpreted to diagnose discontinuities, inclusions, impurities, or cracks in the rotor material.

Since the rotor bore size varies from turbine rotor to turbine rotor, the inspection apparatus 10 must be capable of centering itself in those various sized bores and have transducers which may be radially expanded to engage any bore's wall. After bore wall 16 has been engaged by the transducers and inspection apparatus 10 has been centered, inspection apparatus 10 is rotated about longitudinal axis 18 through a predetermined arc length for each selected axial position in the rotor for which ultrasonic data is desired. While the present invention will be described as used in conjunction with a bored turbine rotor 12, it is to be understood that the present invention may be successfully used for inspection purposes with any circular bore.

Figure 2:
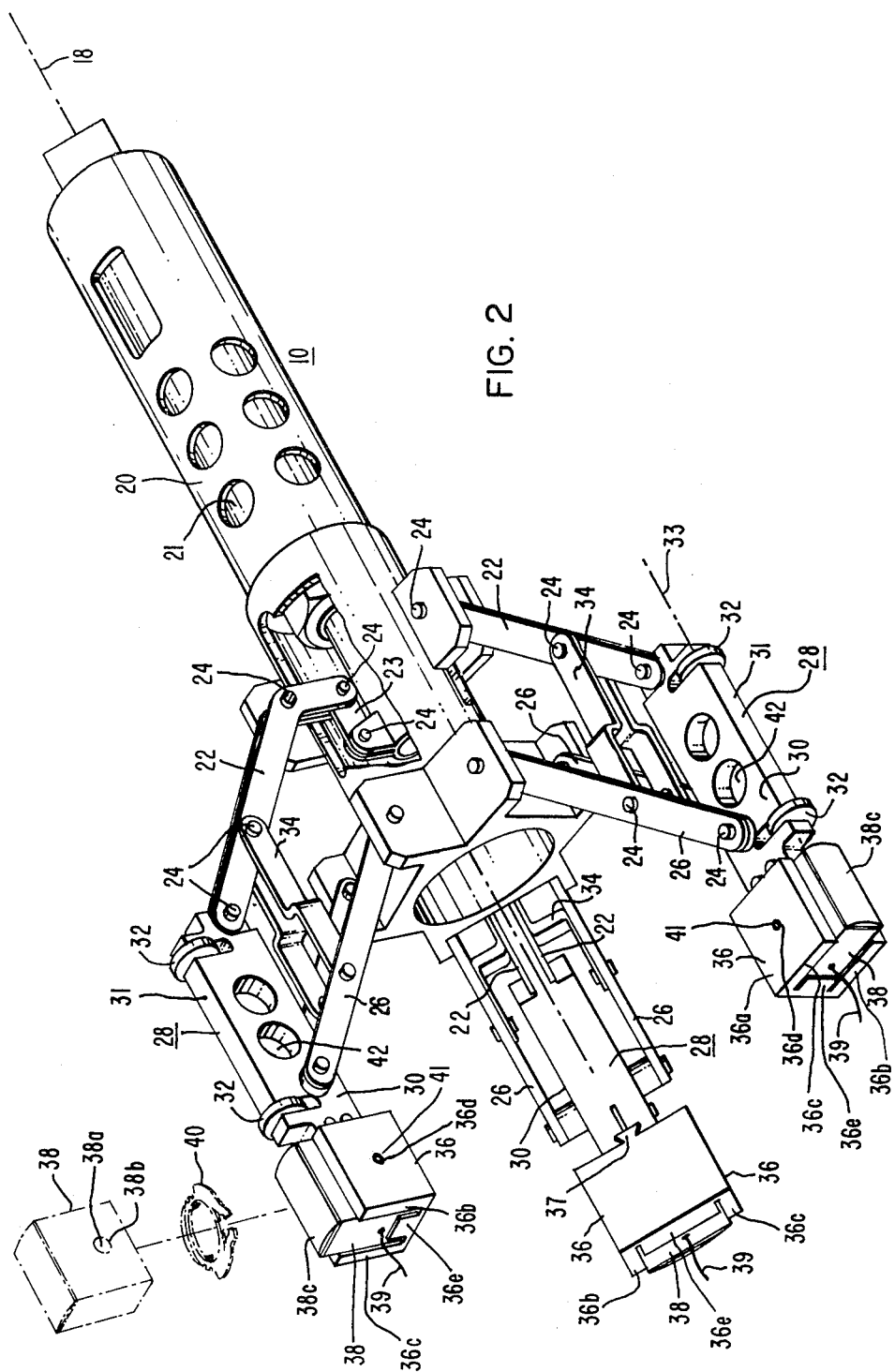
FIG. 2 is an enlarged partial sectional isometric view of the invention illustrated in FIG. 1.

FIG. 2 is an enlarged, partially cut away isometric view of inspection apparatus 10. Housing 20, preferably of tubular shape, houses a pneumatically actuated cylinder 21 which is joined to linkage arms 22 by connecting arms 23. Linkage arms 22 are rotatably connected to housing 20 by pins 24 and are rotatably actuated by axial displacement of cylinder 21 in the desired axial direction along axis 18. Linkage arms 22 are disposed in pairs at three equally spaced circumferential locations and at the same axial position relative to housing 20. The aforementioned circumferentially separated locations are actually circumferentially midway between each pair of linkage arms 22. Each pair of linkage arms 22 is rotatably connected to a support arm structure 28 which includes a central portion 30 and an engagement portion such as wheel 32 which is rotatably joined to central portion 30 along its radially outer boundary 31 and having an axis of rotation 33 parallel to longitudinal axis 18. Although two wheels 32 are preferable for each support arm, one wheel per support would enable the invention to function. Wheels 32 protrude radially beyond central portion 30 so as to insure engagement of bore wall 16 with wheels 32 rather than central portion 30. The axes of rotation for wheels 32 are maintained in a parallel relation with axis of rotation 18 and bore wall 16 by a second plurality (six) of linkage arms 26 which are rotatably connected to support arm structures 28 and housing 20. While wheels 32 are shown, it is to be understood that other engagement portions which are matable with bore wall 16 could be substituted therefor.

Linkage arms 26 are preferably disposed in pairs about the three aforementioned, equally spaced circumferential locations with it being understood that each pair is rotatably connected to the same support arm structure and that the circumferential locations referred to are circumferentially midway between each pair of linkage arms 26. While the second plurality of linkage arms 26 act in concert with linkage arms 22 and are axially separated therefrom by equal distances at the housing 20 and support arm structure 28 (between connecting pins 24) so as to provide a four bar, parallel linkage, it is to be understood that any means for maintaining parallel relation between axis of rotation 33 and bore wall 16 may be used with the present invention and still obtain all the advantages thereof. It is to be further understood that linkage arms 26 of each pair are circumferentially disposed farther apart than linkage arms 22 so as to enable linkage arms 22 to retract within linkage arms 26 when support arm structure 28 is disposed at its minimum radial distance relative to axis 18. Stiffening arms 34 rotatably connect linkage arms 22 to linkage arms 26 to provide additional structural rigidity thereto.

An instrument carrier 36 is attached to each support arm structure 28 preferably by the illustrated friction clamping dovetail slide structure 37. The position of each carrier 36 may be radially adjusted relative to its attached support arm structure and must be positioned radially within the furthest radial protrusion of wheels 32 so as to insure engagement of wheels 32 with bore wall 16 rather than engagement between carrier 36 and rotor bore wall 16. Instruments such as transducers 38 are disposed in carriers 36 and are biased radially outward by a biasing means such as spring 40 which is disposed between each carrier 36 and transducer 38. It is to be understood that alternative means such as pneumatic cylinders or electric motors could be used to bias the transducers 38 radially outward with equal facility.

The transducer carrier 36 preferably comprises transverse portions 36a and 36b which are joined to a bottom portion 36c. At least one of the transverse portions (36a as illustrated) has an opening 36d which is generally alignable with an aperture 38a formed in each transducer 38. Aperture 38a is, by design, larger in the radial direction than opening 36d and pin 41 which is insertable through opening 36d and into aperture 38a. Radial movement of transducer 38 relative to carrier 36 is obstructed beyond the position where the radially inner wall 38b of aperture 38a contacts pin 41. Thus, the radial position of carrier 36, the force of the biasing means (spring constant in the illustrated embodiment) and the radial length of transducer 38 are cooperatively adjustable to ensure engagement force levels between transducer lens 38c and bore wall 16 of approximately 5 to 10 pounds. Such transducer engagement force levels provide greater accuracy in back wall ultrasonic reflections and reduce transducer lens damage during rotation of inspection apparatus 10 in bore 14 as compared to transducer to bore wall engagement force levels of 50–100 pounds commonly used heretofore when the forces for centering the inspection apparatus' on the bore were applied through the transducers. Independent application of the transducer 38—bore wall 16 ultrasonic transmission engagement force and the wheels 32—bore wall 16 apparatus centering engagement force enables the user to apply optimum values of each. In the illustrated embodiment, transverse portions 36a and 36b constitute circumferentially bounding components which together provide the primary restraining force on the transducers 38 during rotation of inspection apparatus 10. Transverse portions 36e constitute axially bounding components which are joined to bottom portion 36c and are radially shorter than transverse portions 36a and 36b to facilitate electrical connections to transducers 38 by cables 39 which supply electrical communication to and from the transducers.

Holes 42 are illustrated as constituting portions of support arm structures 28 and housing 20 and have as a primary purpose weight reduction. It is, however, to be understood that other materials could be substituted for the preferred material of aluminum so as to obtain the advantages thereof. While no pneumatic connection lines are illustrated for the sake of clarity, it is to be understood that double acting pneumatic cylinder 21 must be connected to such fluid sources or be replaced by an equivalent means for rotating linkage arms 22.

It is now apparent that an apparatus for inspecting a circular bore has been provided in which the apparatus' centering force for coaxially aligning the inspection apparatus 10 with the bore's longitudinal axis 18 may be applied independently from the engagement force necessary to transmit ultrasonic signals between transducers 38 and bore wall 16. Independent adjustment of such engagement forces permits simultaneous attainment of optimum transducer bore wall engagement forces and centering wheel-bore wall engagement forces so as to increase the precision and accuracy with which ultrasonic inspections of material bounding a bore may be conducted.

We claim:

1. An inspection apparatus for supporting instruments in a circular bore and engaging the instruments with a desired force against the wall which bounds the bore, said inspection apparatus comprising:
   a housing which is insertable in a bore along the bore's longitudinal axis;
   a first plurality of linkage arms disposed about said housing at a plurality of circumferential locations;
   first means for rotatably connecting said first plurality of linkage arms to said housing at said first plurality of circumferential locations, said first rotatable connecting means restricting movement of said first plurality of linkage arms within radial planes relative to said housing;
   a plurality of support arm structures each including a central portion and an engagement portion for contacting said bore's wall;
   second means for rotatably connecting said first plurality of linkage arms to said support arm structures;
   means for maintaining said support arm structures' engagement portions in parallel relation with said bore's wall to ensure contact with said bore wall;
   a plurality of instruments engageable with said bore wall;
   means joined to each support arm structure for carrying one of said instruments;
   means for biasing said instrument radially outwardly relative to said support arm structures toward said bore wall; and
   means disposed in said housing for rotating said linkage arms.

2. The inspection apparatus of claim 1, said parallel relation maintaining means comprising:
   a second plurality of linkage arms disposed about said housing at said first plurality of circumferential locations;
   third means for rotatably connecting said second plurality of linkage arms to said housing at said circumferential locations, said first and third rotatable connecting means being axially separated by a predetermined distance; and
   fourth means for rotatably connecting said second plurality of linkage arms to said support arm structures, said second and fourth rotatable connecting means being axially separated by a distance equal to said predetermined distance.

3. The inspection apparatus of claim 1 further comprising:
   a third plurality of linkage arms rotatably joined between linkage arms of said first and second pluralities to provide additional rigidity thereto.

4. The inspection apparatus of claim 1 wherein said instrument carrying means is selectively radially displaceable relative to said support arm structures.

5. The inspection apparatus of claim 4 wherein said instrument carrying means' furthest radially outward displacement is radially within said support arm structures' engagement portions.

6. The inspection apparatus of claim 1, said instrument carrying means joined to each support arm structure comprising:
   a bottom portion; and
   a plurality of transverse portions joined to said bottom portion, said transverse portions being radially outside said bottom portion, said bottom and transverse portions defining a structure having an open, radially outer end, said instrument being receivable in said structure and said biasing means being disposable between said instrument and said bottom portion.

7. The inspection apparatus of claim 6, further comprising:
   means for restraining each of said instrument's radially outward movement beyond a predetermined point.

8. The inspection apparatus of claim 7, said restraining means comprising:
   at least one of said transverse portions of each instrument carrying means having an opening therethrough;
   said instrument having an aperture therein with a radially inner boundary, said aperture being alignable with said opening, said aperture being larger in the radial direction than said opening; and
   a pin insertable in said alignable opening and aperture, said pin permitting relative radial movement of said instrument and said instrument carrying means, said pin being engageable with the radially inner boundary of said aperture so as to prevent further radially outer movement of said instrument relative to said carrying means.

9. The inspection apparatus of claim 6 wherein said transverse portions constitute:
   circumferential components which extend substantially radially and are circumferentially separated by said bottom portion; and
   axial components which extend substantially radially, are axially separated by said bottom portion and said circumferential components, said axial components being radially shorter than said circumferential components.

10. The inspection apparatus of claim 1, said engagement portion comprising:
    at least one wheel rotatably joined to said central portion, said wheel protruding radially beyond said central portion and having an axis of rotation parallel said bore's longitudinal axis.

* * * * *